United States Patent [19]

Adams

[11] 4,010,278
[45] Mar. 1, 1977

[54] COMPOSITIONS OF ALKYL 4-[O-(SUBSTITUTED AMINO)PHENYL]-3-THIOALLOPHANATES AND METHODS OF USE

[75] Inventor: Charles De Witt Adams, Newark, Del.

[73] Assignee: E. I. Du Pont de Nemours and Co., Wilmington, Del.

[22] Filed: Apr. 20, 1972

[21] Appl. No.: 245,901

Related U.S. Application Data

[62] Division of Ser. No. 865,984, Oct. 13, 1969, Pat. No. 3,927,069.

[52] U.S. Cl. .............................. 424/309; 424/287; 424/289; 424/294

[51] Int. Cl.$^2$ .......................................... A01N 9/24
[58] Field of Search ........... 424/309, 287, 294, 289

[56] References Cited

UNITED STATES PATENTS 3,943,163  3/1976  Adams .............................. 260/470

*Primary Examiner*—Sam Rosen

[57] ABSTRACT

Various alkyl 4-[o-(substituted amino)phenyl]-3-thioallophanates are useful as fungicides and mite ovicides. An exemplary specie is methyl 4-(o-butyramidophenyl)-3-thioallophanate.

10 Claims, No Drawings ial No. 865,984, filed Oct. 13, 1969 now U.S. Pat. No. 3,927,069.

COMPOSITIONS OF ALKYL 4-[O-(SUBSTITUTED AMINO)PHENYL]-3-THIOALLOPHANATES AND METHODS OF USE

CROSS REFERENCE TO RELATED APPLICATION

This is a divisional of my copending application Ser. No. 865,984, filed Oct. 13, 1969 now U.S. Pat. No. 3,927,069.

BACKGROUND OF THE INVENTION

This invention relates to a group of alkyl 4-(o-aminophenyl)-3-thioallophanates and to methods of using these compounds to prevent to mitigate damage to plants and inanimate organic materials by fungi and mites.

The survival of man has for a long time been dependent in a large measure upon his ability to protect from the various agents of destruction, plants and their products which satisfy his basic needs. With the rapidly increasing population of the world, it becomes imperative that there be continuing great improvements in the efficiency of the materials and the methods employed to provide this protection. These improvements can be in the form of effective control of more kinds of pests or in the form of requiring less material or work. The materials and methods of this invention represent marked advances in both of these possible areas of improvement, as will be explained more fully.

Application of the compounds of this invention by the methods of this invention entirely precludes or reduces damage to plants and inanimate organic materials due to fungi and mites. Fungus mycelia are killed or prevented from developing further by the presence of one or more of the compounds, i.e., the compounds are fungicidal or fungistatic. The compounds further prevent mite populations from expanding or reduce them to a low level or even eliminate them by preventing the normal hatching of their eggs, i.e., the compounds are mite ovicides.

SUMMARY OF THE INVENTION

It has been found that outstanding fungicidal activity can be obtained by applying to the locus of fungus infestation, the compounds represented by the following formula:

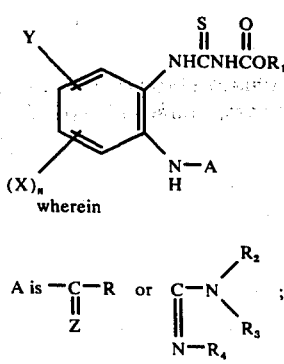

wherein

A is $-\underset{Z}{\overset{\parallel}{C}}-R$ or $\underset{N-R_4}{\overset{R_2}{\underset{\parallel}{C-N}}}$ ;

X is hydrogen, fluorine, chlorine, or bromine;
Y is hydrogen or alkyl of 1 to 4 carbon atoms;
$R_1$ is alkyl of 1 to 12 carbon atoms;
Z is oxygen or sulfur:
R is hydrogen, alkyl of 1 to 12 carbon atoms, alkyl of 1 to 12 carbon atoms substituted with fluorine, chlorine, bromine, alkoxy of 1 to 3 carbon atoms or acetyl; alkoxy of 1 to 4 carbon atoms; or

$R_2$ is hydrogen or methyl;
$R_3$ is hydrogen or alkyl of 1 to 4 carbon atoms;
$R_4$ is hydrogen or methyl;
When Y is alkyl, n is 0 and when Y is hydrogen, n is 1, 2, or 3; and the sodium, potassium, lithium, calcium, barium, copper, zinc and manganese salts of these compounds.

Preferred are those compounds where A is

and more preferred are those compounds where Z is sulfur, X and Y are hydrogen and $R_1$ is methyl, ethyl or isopropyl.

Particularly preferred because of their high order of fungicide activity are:
methyl 4-[o-(3-methylthioureido)phenyl]-3-thioallophanate, and
methyl 4-[o-(3-butylthioureido)phenyl]-3-thioallophanate.

DETAILED DESCRIPTION OF THE INVENTION

The compounds of the invention can be prepared in several ways. They are prepared from alkyl 4-(o-aminophenyl)-3-thioallophanates by the reactors set forth below.

The alkyl 4-(o-aminophenyl)-3-thioallophanates are preferred as described in Application Serial No. 865,964, filed October 13, 1969 by Charles D. Adams, entitled "Alkyl 4-(o-aminophenyl)-3-thioallophanates as Fungicides." In general the preparation of these intermediates involves reacting an o-phenylenediamine with the appropriate alkoxycarbonyl isothiocyanate. The alkoxycarbonyl isothiocyanates can be prepared by the manner described in Bull Chem Soc (Japan) 36, 1214.

Alkyl 4-(o-aminophenyl)-3-thioallophanates react with butyl formate in the presence of p-toluenesulfonic acid to give compounds of type I. This reaction is illustrated by the following equation:

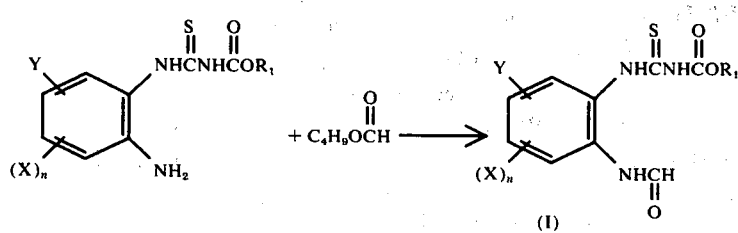

(I)

The alkyl 4-(o-aminophenyl)-3-thioallophanates react with isocyanates and isothiocyanates to give compounds of type II according to the following equation:

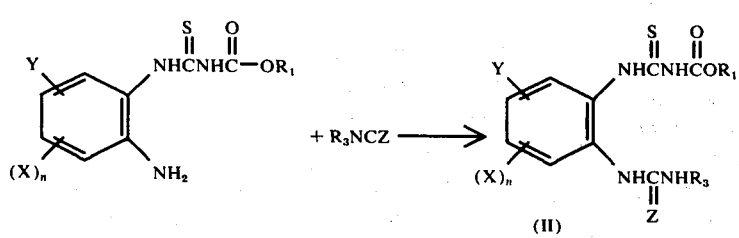

(II)

In this equation Z is oxygen or sulfur.

The intermediate reacts with alkanoic anhydrides to give compounds of type III as set forth by the following equation.

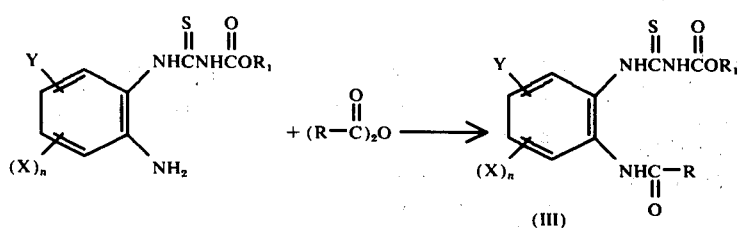

(III)

The intermediate reacts with acid chlorides or carbamoyl chlorides or alkyl chloroformates in presence of an acid acceptor such as triethylamine to give compounds of type IV.

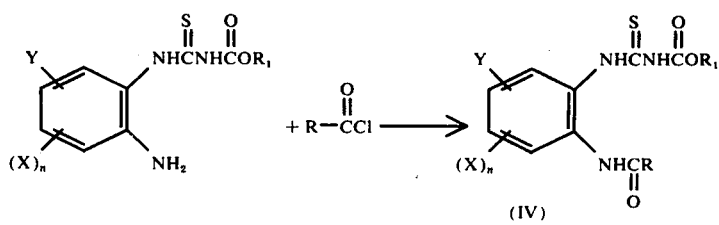

(IV)

In this equation R is alkyl,

or $R_4-O-$.

The reaction with an alkyl-2-thiopseudourea in acetic acid yields compounds of type V according to the following equation:

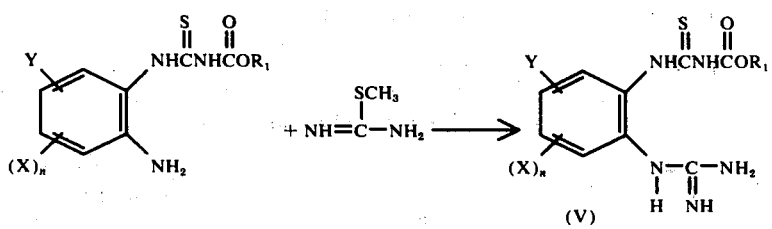

(V)

Reaction with chlorosulfonyl isocyanate, followed by hydrolysis, gives compounds of type VI.

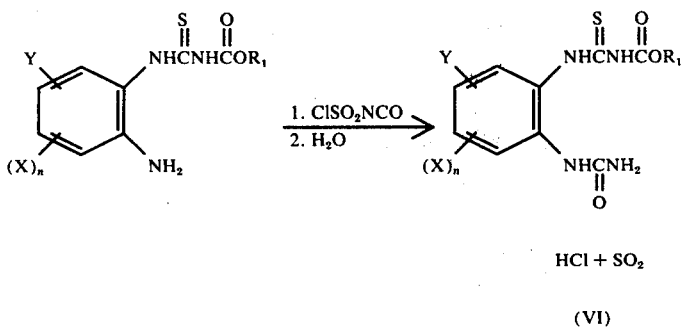

HCl + SO₂

(VI)

In the above equations, X, Y, R, $R_1$, $R_2$, $R_3$, $R_4$, n, and Z are as previously defined.

The alkali metal salts of this invention are prepared by treating the compounds with aqueous sodium hydroxide or potassium hydroxide or an alcoholic solution of lithium methoxide. The salts are isolated by evaporation of the solvent.

The calcium, barium, copper, zinc and manganese salts of this invention are prepared by treating the sodium salt of the appropriate compound with an aqueous solution of an appropriate inorganic metal salt e.g. calcium chloride. The resulting salts are isolated by filtration from the aqueous solution.

The general method of preparation of the compounds of this invention is illustrated by the following examples, the amounts being given in terms of parts by weight unless otherwise specified.

EXAMPLE 1

3 parts of methyl 4-(o-aminophenyl)-3-thioallophanate, 50 parts of butyl formate and 0.5 parts of p-toluenesulfonic acid is refluxed for six hours. The excess butyl formate is removed by evaporation and the resulting solid is washed with water, air-dried and recrystallized from ethanol yielding 1.5 parts of methyl 4-(o-formamidophenyl)-3-thioallophanate, mp-153°–156.5° C.

EXAMPLE 2

11 parts of methyl 4-(o-aminophenyl)-3-thioallophanate in 200 parts of acetone is treated with 10 parts of acetic anhydride. This solution is refluxed for two hours and evaporated. The resulting white solid is washed well with water, air-dried and recrystallized from acetonitrile yielding 8 parts of methyl 4-(o-acetamidophenyl)-3-thioallophanate, mp 193° –195° C. (dec.).

EXAMPLE 3

The following compounds (C) can be synthesized by the method of Example 2 substituting the appropriate alkyl 4-(o-aminophenyl)-3-thioallophanate (A) for methyl 4-(o-aminophenyl)-3-thioallophanate and the appropriate anhydride (B) for acetic anhydride.

COMPOUND 1

A. Methyl 4-(o-aminophenyl)-3-thioallophanate
B. Butyric anhydride
C. Methyl 4-(o-butyramidophenyl)-3-thioallophanate, mp - 193° – 194.5° C.

COMPOUND 2

A. Methyl 4-(o-aminophenyl)-3-thioallophanate
B. Trifluoroacetic anhydride
C. Methyl 4-(o-trifluoroacetamidophenyl)-3-thioallophanate, mp - 186° – 187° C. (dec.).

COMPOUND 3

A. Methyl 4-(o-aminophenyl)-3-thioallophanate
B. Trichloroacetic anhydride
C. Methyl 4-(o-trichloroacetamidophenyl)-3-thioallophanate.

COMPOUND 4

A. Methyl 4-(o-aminophenyl)-3-thioallophanate
B. Bromoacetic anhydride
C. Methyl 4-(o-bromoacetamidophenyl)-3-thioallophanate.

COMPOUND 5

A. Methyl 4-(o-aminophenyl)-3-thioallophanate
B. Dichloroacetic anhydride
C. Methyl 4-(o-dichloroacetamide)-3-thioallophanate mp - 202° C. (dec.).

COMPOUND 6

A. Methyl 4-(o-aminophenyl)-3-thioallophanate
B. Chloroacetic anhydride
C. Methyl 4-(o-chloroacetamidophenyl)-3-thioallophanate, mp - 171°–171.5° C. (dec.).

COMPOUND 7

A. Methyl 4-(o-aminophenyl)-3-thioallophanate
B. methoxyacetic anhydride
C. Methyl 4-(o-methoxyacetamidophenyl)-3-thioallophanate.

COMPOUND 8

A. Methyl 4-(o-aminophenyl)-3-thioallophanate
B. Ethoxyacetic anhydride
C. Methyl 4-(o-ethoxyacetamidophenyl)-3-thioallophanate.

COMPOUND 9

A. Hexyl 4-(o-aminophenyl)-3-thioallophanate
B. Acetic anhydride
C. hexyl 4-(o-acetamidophenyl)-3-thioallophanate.

COMPOUND 10

A. Dodecyl 4-(o-aminophenyl)-3-thioallophanate
B. Acetic anhydride
C. Dodecyl 4-(o-acetamidophenyl)-3-thioallophanate.

COMPOUND 11

A. Methyl 4-(2-amino-4-fluorophenyl)-3-thioallophanate.

B. Propionic anhydride
C. Methyl 4-(4-fluoro-2-propionamidophenyl)-3-thioallophanate.

EXAMPLE IV 7.5 parts of methyl 4-(o-aminophenyl)-3-thioallophanate in 250 parts of acetone is treated with 3.43 parts of diketene and the solution is heated at reflux for two hours. The white solid that is obtained after evaporation of the acetone is recrystallized from acetonetrile yielding 5.2 parts of methyl 4-(o-acetoacetamidophenyl)-3-thioallophanate, mp - 177°–178.5° C. (dec.).

EXAMPLE V 8.0 parts of methyl 4-(o-aminophenyl)-3-thioallophanate in 250 parts of acetone is treated with 3.7 parts of methyl chloroformate and this mixture is refluxed for 2 hours. 3.6 parts of triethylamine is added and reflux is continued for an additional 3 hours. The mixture is cooled and filtered and the filtrate concentrated. The solid obtained and is air-dried. Seven parts of methyl 4-(o-methoxycarbonylaminophenyl)-3-thioallophanate, mp 174°–175° C. (dec.), is thus obtained.

EXAMPLE VI

The following compounds (C) can be synthesized by the method of Example V by substituting the appropriate alkyl 4-(o-aminophenyl)-3-thioallophanate (A) for methyl 4-(o-aminophenyl)-3-thioallophanate and the appropriate alkyl chloroformate or alkanoic acid chloride (B), for methyl chloroformate.

COMPOUND 1

A. Methyl 4-(o-aminophenyl)-3-thioallophanate
B. Tridecanoyl chloride
C. Methyl 4-(o-tridecanamidophenyl)-3-thioallophanate.

COMPOUND 2

A. Methyl 4-(o-aminophenyl)-3-thioallophanate
B. Propyl chloroformate
C. Methyl 4-(o-propoxycarbonylaminophenyl)-3-thioallophanate.

COMPOUND 3

A. Methyl 4-(o-aminophenyl)-3-thioallophanate
B. Butyl chloroformate
C. Methyl 4-(o-butoxycarbonylaminophenyl)-3-thioallophanate.

EXAMPLE VII 5.0 parts of methyl 4-(o-aminophenyl)-3-thioallophanate in 250 parts of acetone is treated with 3.13 parts of chlorosulfonyl isocyanate. This mixture is stirred at room temperature and then is carefully poured into water. The solid is removed by filtration and air-dried, yielding 3 parts of methyl 4-(o-ureidophenyl)-3-thioallophanate, mp 195° C. (dec.).

EXAMPLE VIII 7.5 parts of methyl 4-(o-aminophenyl)-3-thioallophanate in 250 parts of acetone is treated with 2.0 parts of methyl isocyanate and 1 part of triethylamine. This mixture is warmed to 40° for 1 hour and the solvent is evaporated, yielding 7.0 parts of methyl 4-[o-(3-methylureido)phenyl]-3-thioallophanate, mp 194°–195° C. (dec.).

EXAMPLE IX

The following compounds are synthesized by the method of example 8 by substituting the appropriate alkyl 4-(o-aminophenyl)-3-thioallophanate (A) for methyl 4-(o-aminophenyl)-3-thioallophanate and the appropriate alkyl isocyanate or alkyl isothiocyanate (B) for methyl isocyanate.

COMPOUND 1

A. Methyl 4-(o-aminophenyl)-3-thioallophanate
B. Butyl isocyanate
C. Methyl 4-[o-(3-butylureido)phenyl]-3-thioallophanate, mp 180° C. (dec.).

COMPOUND 2

A. Methyl 4-(o-aminophenyl)-3-thioallophanate
B. Methyl isothiocyanate
C. Methyl 4-[o-(3-methylthioureido)phenyl]-3-thioallophanate, mp 156°–158° C. (dec.).

COMPOUND 3

A. Methyl 4-(o-aminophenyl)-3-thioallophanate
B. Butyl isothiocyanate
C. Methyl 4-[o-(3-butylthioureido)phenyl]-3-thioallophanate, mp 176°–178° C. (dec.).

COMPOUND 4

A. Methyl 4-(2-amino-4-chlorophenyl)-3-thioallophanate.
B. Methyl isocyanate
C. Methyl 4-[4-chloro-2-(3-methylureido)phenyl]-3-thioallophanate.

COMPOUND 5

A. Methyl 4-(2-amino-4-bromophenyl)-3-thioallophanate.
B. Methyl isocyanate
C. Methyl 4-[4-bromo-2-(3-methylureido)phenyl]-3-thioallophanate.

COMPOUND 6

A. Methyl 4-[2-amino-4-methylphenyl]-3-thioallophanate.
B. Methyl isocyanate
C. Methyl 4-[4-methyl-2-(3-methylureido)phenyl]-3-thioallophanate.

COMPOUND 7

A. Methyl 4-(4-(2-amino-4-butylphenyl)-3-thioallophanate.
B. Methyl isocyanate
C. Methyl 4-[4-butyl-2-(3-methylureido)phenyl]-3-thioallophanate.

COMPOUND 8

A. Methyl 4-(2-amino-3,5,6-trichlorophenyl)-3-thioallophanate.
B. Methyl isocyanate
C. Methyl 4-[2-(3-methylureido)-3,5,6-trichlorophenyl]-3-thioallophanate.

EXAMPLE X 4.5 parts of methyl 4-(o-aminophenyl)-3-thioallophanate in 200 parts of acetone is treated with 2.2 parts of dimethylcarbamoyl chloride and 1.6 parts of pyridine. This mixture is refluxed for 8 hours, filtered and the solvent evaporated to yield a white solid. This solid is washed well with water and air-dried to yield 4.7 parts of methyl 4-[o-(3,3-dimethylureido)phenyl]-3-thioallophanate.

EXAMPLE XI 4.5 parts of methyl 4-(o-aminophenyl)-3-thioallophanate, 5.56 parts of 2-methyl-2-thiopseudourea sulfate in 250 parts of 70% acetic acid is heated at 100° for 4 hours. This mixture is poured into water and neutralized with sodium bicarbonate to give methyl 4-[o-guanidinophenyl]-3-thioallophanate.

EXAMPLE XII 4.5 parts of methyl 4-(o-aminophenyl)-3-thioallophanate, 6.0 parts of 1,2,3-trimethyl-2-thiopseudourea sulfate in 250 parts of 70% acetic acid is heated at 100° for 4 hours. This mixture is poured into water and is neutralized with sodium bicarbonate to give methyl 4-[o-(2,3-dimethylguanidino)phenyl]-3-thioallophanate.

EXAMPLE XIII 4.5 parts of methyl 4-[o-(3-methylureido)phenyl]-3-thioallophanate is dissolved in 100 parts of water containing 1.2 parts of sodium hydroxide. The aqueous solution is evaporated at reduced pressure to yield the sodium salt of methyl 4-[o-(3-methylureido)phenyl]-3-thioallophanate.

EXAMPLE XIV 4.5 parts of methyl 4-[o-(3-methylureido)phenyl]-3-thioallophanate is dissolved in 100 parts of water containing 1.5 parts of potassium hydroxide. The aqueous solution is evaporated at reduced pressure to yield the potassium salt of methyl 4-[o-(3-methylureido)phenyl]-3-thioallophanate.

EXAMPLE XV 4.5 parts of methyl 4-[o-(3-methylureido)phenyl]-3-thioallophanate is dissolved in 50 parts of methanol containing 0.2 parts of lithium hydride. The methanol is removed at reduced pressure yielding the lithium salt of methyl 4-[o-(3-methylureido)phenyl]-3-thioallophanate.

EXAMPLE XVI 4.5 parts of methyl 4-[o-(3-methylureido)phenyl]-3-thioallophanate is dissolved in 50 parts of 5% sodium hydroxide. 3.0 parts of calcium chloride dihydrate dissolved in 30 parts of water is added to the solution. The calcium salt of methyl 4-[o-(3-methylureido)phenyl]-3-thioallophanate is removed by filtration.

EXAMPLE XVII

The following compounds (C) can be synthesized by the method of Example XVI substituting the appropriate alkyl 4-[o-(alkyl, dialkylureido or thioureido)phenyl]-3-thioallophanate (A) and the appropriate inorganic metal salt (B) for calcium chloride dihydrate.

COMPOUND 1

A. Methyl 4-[o-(3-methylureido)phenyl]-3-thioallophanate.
B. Barium chloride
C. Methyl 4-[o-(3-methylureido)phenyl]-3-thioallophanate, barium salt.

COMPOUND 2

A. Methyl 4-[o-(3-methylureido)phenyl]-3-thioallophanate.
B. Cupric sulfate pentahydrate
C. Methyl 4-[o-(3-methylureido)phenyl]-3-thioallophanate, copper(II) salt.

COMPOUND 3

A. Methyl 4-[o-(3-methylthioureido)phenyl]-3-thioallophanate.
B. Zinc chloride
C. Methyl 4-[o-(3-methylthioureido)phenyl]-3-thioallophanate, zinc salt.

COMPOUND 4

A. Methyl 4-[o-(3-methylthioureido)phenyl]-3-thioallophanate.
B. Manganese chloride
C. Methyl 4-[o-(3-methylthioureido)phenyl]-3-thioallophanate, manganese(II) salt.

As mentioned previously, it has been found that the compounds of the invention possess outstanding fungicidal and mite ovicidal activity when employed to prevent or mitigate damage to plants and inanimate organic materials. The paragraphs which follow describe in more detail the utility of this invention.

The compounds of the invention control a wide variety of fungus diseases of foliage, fruit, stems and roots of growing plants without damage to the host. Fruits, tubers, bulbs, roots, seeds and other plant parts harvested for food, animal feed or for other purposes are protected from fungus deterioration during processing, distribution and storage. Seeds, tubers, cuttings and other plant propagation materials are protected from fungus attack during handling and storage, as well as in the soil after planting. Wood, fabric, fiber board, paper and other industrial materials are protected from unsightly stain and destructive decay caused by fungi. Luggage, shoes, shower curtains, carpets, mats, clothing and other useful household, public or industrial items are protected from rot, fungus stains and mold growth. Painted surfaces are protected from stain and discoloration by incorporation of a compound of this invention in the paint formulation.

The many fungi against which the compounds of this invention are active may be represented by, but is not intended to be limited to, the following: *Venturia inaequalis*, which causes apple scab; *Podosphaera leucotricha*, which causes powdery mildew on apple; *Uromyces phaseoli*, which causes bean rust; *Cercospora apii*, which causes early blight of celery; *Cercospora beticola*, which causes leaf spot of sugar beats; *Sclerotinia sclerotiorum*, which causes rot of vegetable crops, such as lettuce, beans, carrots, and celery; *Colletotrichum* spp., which cause anthracnose of fruits and vegetables, such as beans, tomatoes and coffee; *Septoria apii*, which causes late blight of celery; *Mycosphaerella musicola*, which causes Sigotoka disease of banana; *Piricularia* sp., which causes Johnson spot on banana; *Erysiphe cichoracearum*, which causes powdery mildew on cantaloupe and other cucurbit crops; *Penicillium digitatum*, *Phomopsis* spp., and *Dipoldia natalensis*, which cause fruit rots on citrus; *Ceratostomella ulmi*, which causes Dutch elm disease; *Sphaerotheca humuli*, which causes powdery mildew on roses; *Diplocarpon rosae*, which causes black spot on roses; *Rumularia* sp., which causes leaf spots on ornamental plants; *Botrytis cinerea*, which causes blossom and fruit rots of ornamentals, fruits and vegetables; *Uncinula necator*, which causes powdery mildew on grapes; *Guignardia bidwellii*, which causes grape black rot; *Melonconium fuligineum*, which causes white rot on grapes; *Coccomyces hiemalis*, which causes cherry leaf spot; *Cytospora* sp., which cause cankers of trees; *Cladosporium carpophilum*, which causes peach scab; *Fusicladium effusum*, which causes pecan scab; *Erysiphe graminis*, which causes powdery mildew on cereals; *Monolinia Sclerotinia*) *laxa* and *M. fructicola*, which cause brown rot on stone fruits, such as peaches, cherries and apricots; *Pseudopeziza ribes, which causes leaf spot on gooseberry; Piricularia oryzae*, which causes rice blast; *Puccinia glumarum P. coronata* and *P. glumarum*, which cause leaf rusts of wheat, oats and grasses, respectively; *Puccinia graminis tritici*, which causes stem rust of wheat; *Claviceps purpurea*, which causes ergot of rye and grasses; *Aspergillus niger, which causes cotton boll rot as well as decay following wounding in many plant tissues; Aspergillus flavus*, which causes mold growth on peanuts, as well as on other food and field materials; *Aspergillus terreus*, which is common in soil and attacks vegetable matter; *Tilletia caries* and other *Tilletia* species, which cause common bunt of wheat; *Ustilago tritici, Ustilago nigra, Ustilago avena* (and other *Ustilago* species), which cause loose smut of wheat, barley, and oats, respectively; *Urocystis tritici* and other *Urocystis* species, which cause loose smut of wheat; *Sphaecelotheca sorghi*, which causes covered smut of sorghum; *Ustilago hordei* and *Ustilago kolleri*, which cause covered smut of barley and oats, respectively; *Pithomyces chartorum*, which is present in turf, pastures, and other grassy areas and is known to have several secondary effects; *Gloeodes pomigena*, which causes sooty blotch on apples; *Physalospora obtusa*, which causes black rot on apples; *Microthyriella rubi*, which causes flyspeck on apples; various species of Rhizoctonia, Fusarium and Verticillium present in soil and attacking the roots or other underground parts and the vascular system of a variety of plants; various species of Penicillium growing on such things as fabric, fiber board, leather goods and paint; species of Myrothecium attacking such items as shower curtains, carpets, mats and clothing.

The mite ovicidal action of the compounds of this invention is useful in preventing the development of damaging populations of mites or in causing the gradual reduction of existing populations. The movement of mites is limited. Thus, an increase in population or the continuation of a high population in a particular locus depends largely upon the hatching of eggs laid in that locus.

Mite eggs do not hatch to produce living young if these eggs are treated with one of these compounds, or if they are laid on a surface containing one of these compounds. Further, the eggs will not hatch if they are laid by a female mite that has been in contact with one of these compounds, or are laid by a female mite that is ingesting or has recently ingested food such as plant juices containing one of these compounds. This interference with the hatching of eggs prevents the population from increasing significantly beyond that present at the time of treatment. Also, this ovicidal action, along with the high natural mortality of adults, can largely eliminate mites from an already infested area over a relatively short period of time. Further, as long as the compounds are present on the surface, the mites occupy or remain in their food supply, new populations cannot develop.

Many species of mites which cause damage to fruits, field crops, vegetables, and ornamentals under a wide variety of circumstances are controlled by the compounds and methods of this invention. The extent of the practical utility of the mite control obtained is represented by, but is not intended to be limited to, the following listing of specific susceptible mites along with the types of damage that they can cause: *Panoncychus ulmi* (European red mite) and *Tetranychus telarius* (two-spotted mite) which are commonly called "orchard mites"; these mites attack a great many deciduous tree fruits including apples, pears, cherries, plums and peaches; *Tetranychus atlanticus* (Atlantic or strawberry mite), *T. cinnabarinus* (carmine spider mite) and *T. pacificus* (Pacific mite); these mites attack cotton and numerous other crop plants; *Paratetranychus citri* (citrus red mite) and others which attack citrus; *Byrobia praetiosa* (clover mite) which attacks clover, alfalfa and other crops; *Phylocoptruta oleivora*, the citrus rust mite; *Aceria neocynodomis* which attacks grasses and other plants; *Tyrophagus lintneri* which is a serious pest in stored foods and on cultivated mushrooms and *Lepidoglyphus destructor* which injures Kentucky bluegrass seed in storage.

The compounds of this invention when applied by certain of the methods of this invention enter and move freely within plants, i.e., they are systemic. Thus both fungi and mites can be controlled in plants in parts well removed from the point of application. In view of this activity, the compounds can be applied to seeds; thus the treatment of cucumber seeds with a few grams per 50 kilograms of seed of a compound of this invention provides control of powdery mildew (*Erysiphe cichoracearum*) and spider mites such as *Tetranychus urticae* on the resulting plants for periods in excess of 40 days. Applications to soil also provides control of certain foliage diseases and mites on plants growing in the treated soil. Spray or dust treatments of plant foliage and stems impart protection against both fungi and mites to other parts of the plant not actually sprayed and to new foliage developing later.

There are important practical advantages associated with the use of an effective systemic pesticide. Thus successful application to seed as described above, results in great savings in chemical and application costs. Soil applications which effectively protect entire plants for an extended period also represent similar savings. Distribution within the plant following foliage treatment eliminates the need for frequent retreatment to protect rapidly growing tissue. Also, materials within the plant are not subject to removal by rainfall. Similarly, movement or translocation of the chemical within the plant can provide protection to those parts of the plant that may not have been covered by the original spray application. This is of particular importance with plants of dense growth character resisting the intrusion of the spray and also to tall plants, such as shade trees, where the spray will not reach to the top.

An additional valuable characteristic of the compounds of this invention is their ability to prevent the spread or to kill fungus infection already established within a plant, i.e. they are curative. Thus, the compounds need not be applied until after conditions develop which permit the actual initiation of fungus attack. This means that, under some circumstances, it is possible to avoid applying any chemical during the entire life of the crop. In other cases, only a part of the normal full schedule of pesticide is required.

Therefore, great savings both in chemical cost and application labor are possible with compounds capable of systemic and curative performance. Another saving is afforded by the compounds of this invention through the fact that both fungi and mites are controlled by applications of a single chemical.

The compounds of this invention provide protection from damage caused by fungi, mites or both when applied to the proper locus by the methods described hereinafter and at a sufficient rate to exert the desired fungicidal and mite ovicidal effect. The rates which will give the desired effect will be labeled a pesticidally effective amount. They ae especially suited for the protection of living plants such as fruit-bearing trees, nut-bearing trees, ornamental trees, forest trees, vegetable crops, horticultural crops (including ornamentals, small fruits and berries), fiber crops, grain and seed crops, sugarcane, sugar beets, pineapple, forage and hay crops, beans, peas, soybeans, peanuts, potatoes, sweet-potatoes, tobacco, hops, turf and pasture.

Living plants may be protected from fungi and mites by applying one or more of the compounds of this invention to the soil in which they are growing or in which they may subsequently be seeded or planted; or to seeds, tubers, bulbs or other plant reproductive parts prior to planting; as well as to foliage, stems and fruit of the living plant. Living plants can also be protected by dipping the root system or physically injecting the chemical or chemicals into roots or stems.

Soil applications are made from dusts, granules, pellets, slurries or solution. Preferred rates for application of the compounds of this invention to soil in which plants are or will be growing range from 0.01 to 500 parts per million by weight of the soil in which the roots are or will be growing. More preferred use rates are in the range of 0.1 to 50 parts per million, and the most preferred rates are in the range of 0.25 to 25 parts per million.

Preferred rates for application to seeds, tubers, bulbs or other plant reproductive parts, range from 0.03 to 6000 grams of active compound of this invention per 50 kilograms of planting material treated. More preferred rates are in the range of 0.3 to 3000 grams of active compound per 50 kilograms. The most preferred rates are in the range of 2.8 to 1500 grams per 50 kilograms.

Applications are made from dusts, slurries or solutions. Such treatments protect the treated parts themselves from damage due to fungi, mites, or both, and in addition, impart extended protection against both types of pests to the resulting new plants.

Preferred rates for application of the compounds of this invention to foliage, stems and fruit of living plants range from 0.012 to 60 kilograms of active ingredient per hectare. More preferred rates are in the range of 0.025 to 30 kilograms per hectare and the most preferred rates are in the range of 0.05 to 15 kilograms per hectare. The optimum amount within this range depends upon a number of variables which are well known to those skilled in the art of plant protection. These variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries or solutions.

Preferred rates for dip applications to roots of living plants are in the range of 0.5 to 18,000 grams of active ingredient per 380 liters of water or other liquid carrier. More preferred rates are in the range of 4.5 to 9,000 grams per 380 liters and the most preferred rates are in the range of 45 to 4500 grams per 380 liters.

Preferred rates for injection into the roots or stems of living plants are in the range of 0.01 to 10,000 parts per million of water or other liquid carrier. More preferred rates are in the range of 0.1 to 5,000 parts per million. The most preferred rates are in the range of 1 to 1,000 parts per million.

Plant parts such as fruits, tubers, bulbs, foliage roots and the like, harvested for food or feed, are protected from decay and other deterioration caused by fungi or mites during processing, distribution and storage by treatment with an active compound of this invention. The plant parts to be so protected can be dipped in a liquid bath containing the active ingredient, dusted with a finely divided preparation of the active ingredient, sprayed, misted with an aerosol containing the compound, or enclosed in wrapping or packing materials inpregnated with the active compound.

If a liquid bath is used, it can contain an amount of the active ingredient in the range of 1 to 5,000 parts per million of the weight of the fluid. A more preferred range for the bath is 5 to 2,500 parts per million, and the most preferred range is 10 to 1,000 parts per million.

Dusts as well as wrapping or packing materials used for this type of application can contain 0.01 to 10% of the active ingredient. More preferred rates are in the range of 0.1 to 5% and the most preferred rates are in the range of 0.2 to 2.5%.

Wood, leather, fabric, fiber board, paper and other industrial materials of an organic nature can be protected from decomposition or discoloration by fungi and infestation by mites by coating, incorporating or impregnating with an effective amount of one or more of the compounds of this invention. The coating can be accomplished by dipping, spraying, flooding, misting (as with an aerosol) or dusting the material to be protected with a suitable composition containing the active ingredient. The preferred use rates for the active ingredient in the treating preparation actually applied to the material to be protected are in the range of 0.025 to 95% by weight. More preferred rates are in the range of 0.05 to 50%, with the most preferred rates being in the range of 0.1 to 25%.

Where incorporation or impregnation procedures are to be employed, use rates may be expressed in terms of the amount of active ingredient introduced into the material to be protected. The preferred use rates for these types of applications are in the range of 0.001 to 30 percent by weight of active ingredient in the final product. More preferred rates being in the range of 0.01 to 7%.

Luggage, shoes, shower curtains, carpets, mats, clothing and other useful household, public or industrial items are protected from rot, fungus stains and unsightly mold growth as well as infestation by mites by the active compounds of this invention. Again, either surface or deep protection can be obtained. Surface treatment is by dips, washes, sprays, aerosols or dust applications. Deep treatment is accomplished by penetrating solutions. Sprays, dips and washes contain the active compound of the invention at rates of 10 to 5000 parts per million. Fluids for aerosol application and dusts contain 0.1 to 20% weight. Penetrating solvent solutions contain an amount of the active ingredient that results in a deposit of 5 to 20,000 parts per million in the material to be protected.

Painted surfaces can be protected from unsightly stain and mold growth by incorporating in the paint formulation, prior to application, 5 to 20,000 parts per million of an active compound of this invention. More preferred rates are in the range of 10 to 10,000 parts per million and the most preferred rates are in the range of 20 to 5,000 parts per million. Such treatments with the compounds of this invention also protect the paint while still in the can from deterioration by fungi.

Damage by mites to stored organic products such as grain, seed, bulbs, tubers, meat or animal hides is kept to a minimum by treating the floors, walls, portions, and other parts of warehouses or other structures with one or more of the active compounds. Applications are made by the use of dusts, sprays, or aerosols with preferred use rates in the range of 0.05 to 1000 grams of the active compound of this invention per 93 square meters of surface to be kept free of excessive mite populations.

As was previously set forth, the compounds of this invention are especially suited for use on living plants. Application to the foliage, stems and fruit of plants at the rate indicated above is generally accomplished by employing sprays, dusts or aerosols containing the proper amount of active ingredient. For the control of mites and fungi which are generally present, applications often start prior to the time that the problem actually appears and continue on a pre-determined schedule. Such a procedure is termed "preventive" or "protective".

With the compounds of this invention, successful control of plant diseases can also be accomplished by applications made after they are present. Fungus mycelia within the plant tissue are actually killed. This approach or effect is termed "curative" or "eradicant" and permits the user to realize considerable savings.

Curative control of plant diseases with the compounds of this invention is enhanced if the treated plant parts are moist for one or more periods of 2 to 12 hours each soon after the active compound is applied. Often the slow drying of an original spray treatment or naturally occurring rains, mists, fogs or dews will accomplish this. Under other circumstances, such as during dry periods or in shelters such as greenhouses, it is necessary to keep the plants moist by some special effort for best results.

When the compounds of this invention are applied, their activity can be enhanced by using certain adjuvants, for example in the water in which the fungicide is dispersed. These adjuvants may be surface-active agents, oils, humectants, enzymes, carbohydrates, and organic acids. They improve the performance on tubers, on foliage, in treatments used for dip application to roots of living plants, in liquids used for injection into the roots or stems of living plants, or in mixtures used to treat fruits, tubers, bulbs, roots and the like after harvest.

The pressures of an expanding world population, together with the need for more economical agricultural practices have resulted in earlier harvesting of grains, including corn. Frequently the grain is stored or sold to grain elevators without proper drying. Spoilage of the grain under these conditions may be quite rapid, with the formation of toxins and other substances that are very harmful or fatal when fed to animals.

Safe, effective feed additives that combat spoilage are thus of great importance to agriculture.

The compounds of this invention can be used to prevent the spoilage of animal feeds. In particular, when mixed with the feed, they provide more efficient and longer lasting protection without harm or injury to livestock that consume it. The compounds of this invention may be conveniently formulated for this use in a number of the ways previously disclosed and these formulations may be mixed directly with mixed feed, newly harvested hay and newly harvested grain. These compounds effectively prevent the spoilage of corn, sorghum, wheat, barley, oats, rye and other grains that may be used as livestock feed.

Under normal conditions, these compounds may be incorporated into feeds at rates of from 0.01% to 0.25% with excellent results. Higher rates may be required under very damp conditions.

COMPOSITIONS

Compositions of this invention are formulated by mixing a compound of this invention with one or more agricultural adjuvants, e.g. surface active agents.

The surface active agents used in this invention can be wetting, dispersing or emulsifying agents. They may act as wetting agents for wettable powders and dusts, as dispersing agents for wettable powders and suspensions and as emulsifying agents for emulsifiable concentrates. Surfactants also enhance the biological activity of the compounds of this invention. Such surface active agents can include such anionic, cationic and nonionic agents as have heretofore been generally employed in plant control compositions of similar type. Suitable surface active agents are set out, for example, in "Detergents and Emulsifiers Annual — 1968" by John W. McCutcheon, Inc. Other surface active agents not listed by McCutcheon but still effective dispersants by virtue of protective colloid action include methyl cellulose, polyvinyl alcohol, hydroxyethylcellulose, and alkyl substituted polyvinylpyrrolidones.

Suitable surface active agents for use in compositions of this invention include polyethylene glycol ethers with fatty and rosin acids, polyethylene glycol ethers with alkyl phenols or with long-chain aliphatic alcohols, polyethylene glycol ethers with sorbitan fatty acid esters, and polyoxyethylenethio ethers. Other suitable surfactants include amine, alkali and alkaline earth salts of alkyl aryl sulfonic acids; amine, alkali and alkaline earth fatty alcohol sulfates; dialkyl esters of alkali metal sulfosuccinates; fatty acid esters of amine, alkali and alkaline earth isethionates and taurates; amine, alkali and alkaline earth salts of lignin sulfonic acids; methylated or hydroxyethylated cellulose; polyvinyl alcohols; alkyl substituted polyvinylpyrrolidone; amine, alkali and alkaline earth salts of polymerized alkylnaphthalene sulfonic acids; and long-chain quaternary ammonium compounds. Anionic and nonionic surface active agents are preferred.

Among preferred wetting agents are sodium alkylnaphthalene sulfonates, sodium dioctylsulfosuccinate, sodium dodecylbenzene sulfonate, ethylene oxide condensates with alkylated phenols such as octyl-, nonyl- and dodecylphenol, sodium lauryl sulfate, and trimethylnonyl polyethylene glycols. Among preferred dispersing agents are sodium, calcium and magnesium lignin sulfonates, low-viscosity methyl cellulose, low-viscosity polyvinyl alcohol, alkylated polyvinylpyrrolidone, polymerized alkylnaphthalene sulfonates, sodium N-oleyl or N-lauryl isethionates, sodium N-methyl-N-palmitoyl taurate and dodecylphenol polyethylene glycol esters.

Among preferred emulsifying agents are ethylene oxide adducts of lauric, oleic, palmitic or stearic acid esters of sorbitan or sorbitol; polyethylene glycol esters with lauric, oleic, palmitic, stearic or rosin acids; oil-soluble alkylarylsulfonates; oil-soluble polyoxyethylene ethers with octyl, nonyl and dodecylphenol; polyoxyethylene adducts to long-chain mercaptans, and mixtures of these surfactants.

In general, less than 10% by weight of the surface-active agent will be used in compositions of this invention and ordinarily the amount of surface-active agents will range from 1-5% but may even be less than 1% by weight.

Additional surface-active agents can be added to the above formulation to increase the ratio of surfactant-to-active agent up to as high as 5:1 by weight. Normally the purpose of adding higher amounts of surfactant is to increase the fungicidal effect of the active compounds. When used at higher rates it is preferred that the surfactant be present in the range of one-fifth to five parts surfactant for each one part of active agent.

Compositions of this invention will contain, in addition to surface-active agents, other agricultural adjuvants such as solid or liquid diluents to produce wettable powders, dusts, granules or liquid formulations as desired.

A. WETTABLE POWDERS

Wettable powders are compositions which usually contain inert solid diluents in addition to surfactants. These inert diluents may serve several purposes. They can act as grinding aids to prevent mill smear and screen blinding, they can aid rapid dispersion of the mix when placed in water, they can absorb liquid or low melting solid active material to produce a free-flowing solid product, they can prevent agglomeration into lumps upon prolonged hot storage and they can permit preparation of compositions with a controlled amount of active ingredient so that proper dosage is easily measured by the consumer.

Suitable diluents may be either inorganic or organic in origin. These include the natural clays, diatomaceous earth, synthetic mineral fillers derived from silica or silicates, insoluble salts produced by precipitation in fluffy form such as tricalcium phosphate or calcium carbonate, and powdered organic diluents such as shell flours, wood flours, corn cob flour or sucrose. Preferred fillers for the compositions of this invention include kaolin clays, attapulgite clay, nonswelling calcium, magnesium montmorillonites, synthetic silicas, synthetic calcium and magnesium silicates, diatomaceous silica, corn cob flour and sucrose.

Wettable powders will normally contain both a wetter and a dispersant. Most preferred for dry wettable powders are those anionic and nonionic surfactants which exist in solid form. Occasionally a liquid, nonionic surfactant, normally considered an emulsifying agent can be used to produce both wetting and dispersion.

Wetting and dispersing agents in wettable powders of this invention, when taken together, will comprise from about 0.5 weight percent to 5.0 weight percent of the total composition. The active component will be present at a concentration of from about 25% to 99% and diluent makes up the balance of 100%. Where needed a corrosion inhibitor or foaming inhibitor may be added at rates of 0.1% to 1.0% with a corresponding reduction in diluent.

B. DUSTS

Dust compositions are those intended for application in dry form with suitable dusting equipment. Since wind drift is undesirable when applying dusts, the most suitable dust diluents are those which are dense and rapid settling. These include kaloinites, talcs, pyrophyllites, ground phosphate rock, Sericite, and ground tobacco stems. However, dusts are usually most easily prepared by diluting an existing high-strength wettable powder with a diluent so that the final dust will frequently contain a fraction of light, absorptive diluent as well as a denser filler.

A wetting agent is desirable in dust formulations so that adhesion to dew-covered foliage is enhanced. Dusts made from wettable powders will usually contain sufficient wetter, but dusts made directly from unformulated active will usually contain an added wetting agent. Dry solid anionic or nonionic wetters are preferred.

Dust formulations will normally contain from 2.0 weight percent to 25 weight percent of active material, from 0.005% to 1.0% wetting agent, and from 3% to 20% light grinding aid diluent and the balance dense, rapid settling diluents. If made by diluting a prepared wettable powder it will also contain a small amount of dispersing agent which has no active role when the composition is used as a dry dust.

C. EMULSIFIABLE LIQUIDS

Emulsifiable liquids are formulated by combining the compounds of this invention with a suitable emulsifier and an organic liquid with low water solubility. The active component may be completely dissolved in the organic liquid or it may be a finely ground suspension in a nonsolvent liquid. Suitable organic liquids include alkylated naphthalenes, xylene, high molecular weight ketones such as isophorones, dibutyl or diamyl ketone, esters such as amyl acetate and normal or iso paraffins. Most preferred emulsifiers are blends of oil soluble sulfonates and nonionic polyoxyethylene glycol esters or ethers of fatty acids or alkylated phenols.

The active component in emulsifiable concentrates will be present at from 10 weight percent to about 40 weight percent. Combined emulsifiers will be present at from 3 weight percent to about 10 weight percent and the balance will be an organic carrier liquid or solvent.

D. GRANULES

Soil treatments with fungicides, either pre- or post-emergence can frequently be mose readily applied with granules. Granular products, with the compounds of this invention, can be made in a number of ways. The active materials can be melted or dissolved in a volatile carrier and sprayed upon preformed granules. They may be mixed as powders with suitable diluents and binders, then moistened and granulated followed by drying. Powders may also be applied to coarsely porous granules by tumbling together and applying some nonvolatile liquid such as oil, glycol or a liquid non-ionic surfactant to act as a binder. Rates of granule disintegration and dispersion of active material in moist soil can be controlled by choice of added surfactants or selection of the binder used to form the granule.

Suitable preformed granules include those made from attapulgite clay, granular expanded vermiculite, ground corn cobs, ground nut shells or preformed kaolinite granules. When active fungicide is placed upon such carriers the concentration may range from 1% to 25%. However, unless applied from a molten state, it is difficult to prevent segregation of active and carrier in concentration ranges above about 10% on preformed granules. When higher concentrations of active are desired best results are obtained by premixing powdered active, diluents, binders and surfactants, then granulating so that the active is distributed throughout the granule and not solely upon its surface. Granulation can be accomplished by tumbling or extrusion of a wet mass, followed by drying, and if necessary size reduction, and finally sieving.

Suitable diluents for the preparation of granules by granulation or extrusion include kaolin clays, sucrose, nonswelling calcium-magnesium montmorillonites, and gypsum. Cohesion to a firm granule is usually obtained by moistening, compacting and drying, with or without some binding agent. Kaolin clays form firm granules if bound together with gelatinous agents such as methylcellulose, natural gums or swelling bentonite. Calcium-magnesium bentonites require no binder, and gypsum can be made to form firm granules with either the addition of plaster of Paris or certain salts such as ammonium sulfate, potassium sulfate or urea which form double salts with gypsum.

The active content of formed granules can range from 1–90% although 75% active represents about the upper level if controlled disintegration of the granule in moist soil is desired. Control of disintegration rate is attained by controlled compaction, e.g., controlled extrusion pressure or by the addition of inert water-soluble components such as sodium sulfate or sugar which can leach away.

E. AQUEOUS DISPERSIONS

Aqueous dispersions of fungicides may be preferred to wettable powders where minimum agitation is available in application equipment and accurate dosage is essential. Even the best and finest wettable powder will not disperse completely in water. Small agglomerates remain which settle rapidly. However, when a solid is ground in a water phase, in the presence of dissolved surfactants, each particle develops an adsorbed layer that repels its neighbors and complete dispersion is maintained. This will still not prevent a slow settling to the bottom of stored containers with the formation of a dense "clay" that is difficult to resuspend. A practical aqueous dispersion concentrate must be free from "claying" during an extended shelf life. Certain acrylic acid polymers and sheared hydrated attapulgite will effectively prevent claying.

Suitable aqueous dispersion of the compounds of this invention are prepared by pebble milling or sand milling the active ingredient, one or more dispersants and an anticlaying component in water until the active particle size is less then 10 microns, preferably less than 5 microns. In climates where freezing is a problem, mixtures of glycols and water may be used as the continuous phase.

F. AQUEOUS SOLUTIONS AND WATER SOLUBLE POWDERS

Aqueous solutions and water soluble powders may also be preferable to other formulations intended for application in liquid form. The alkali metal salts of the active ingredients of this invention are soluble in water and other polar solvents such as lower alcohols, glycols, ketones and the like. Concentrates suitable for dilution with water may be prepared by addition of the required quantity of alkali metal hydroxide to the slurry of active compound in one or more of the above solvents. Alternatively, the alkali metal salt thus formed may be isolated as a solid which is then formulated as a water soluble powder, using water-soluble salts and small amounts of anti-caking agents as diluents.

G. LOW VOLUME APPLICATIONS

While conventional applications of sprayable formulations have usually been made in a dilute form (for example at a rate of about 200 liters per hectare or more), the compounds of this invention can also be applied at higher concentrations in the typical "ultra-low-volume" or "low-volume" applications from aircraft or ground sprayers. For this purpose wettable powders can be dispersed in small amounts of aqueous or nonaqueous carriers and the suspension or emulsifiable concentrates can be used directly or with minor dilution. Special compositions, particularly suitable for ULV applications are solutions or finely divided suspensions in one or more carriers such as dialkylformamides, N-alkylpyrrolidones, dimethylsulfoxide, water, esters, ketones, glycols, glycol ethers and the like. Other suitable carriers include aromatic hydrocarbons (halogenated and non-halogenated), aliphatic hydrocarbons (halogenated and non-halogenated) and the like.

The compositions of the invention can contain, in addition to the active ingredient of this invention, conventional insecticides, miticides, bactericides, nematocides, fungicides, or other agricultural chemicals such as fruit set agents, fruit thinning compounds, fertilizer ingredients and the like, so that the compositions can serve useful purposes in addition to the control of fungi and mite infestations.

The additional agricultural chemicals are employed in mixtures or combinations of amounts ranging from one-fifth to twenty times that of the compound or compounds of this invention. The proper choice of amounts is readily made by one skilled in the art of protecting plants from pest depredations.

In order that the invention may be better understood, the following examples are given in addition to those above. All parts are parts by weight unless otherwise indicated.

WETTABLE POWDERS

| Wettable Powders | |
|---|---|
| Example 18 | Percent |
| Methyl 4-(o-methoxycarbonylaminophenyl)-3-thioallophanate | 50 |
| alkylnaphthalenesulfonic acid, sodium salt | 1 |
| low viscosity methyl cellulose | 0.5 |
| Kaolin clay | 48.5 |

The ingredients are combined, mixed, micropulverized, air milled and then blended. The resulting powder wets and disperses readily in water and is suitable for application in normal spray equipment. Any of the other thioallophanates mentioned above may be substituted for the active ingredient here to give useful wettable powders.

The above 50% wettable powder formulation is dispersed in water to give an active ingredient concentration of 1,000 ppm in water. Eight uniform apple trees of the same variety are selected for testing. Four of these are sprayed to run-off, which is approximately 2850 liters per hectare, at weekly intervals during the growing season with the above formulation, and the other four trees are left unsprayed.

By the end of the season the unsprayed trees have developed very high populations of orchard mites and are highly infected with apple scab, *Venturia inaequalis*. Due to the feeding of the mites, the foliage is russeted and drops prematurely. Also the untreated trees have poor twig growth and small, spotted fruit. The trees sprayed with the formulation of this example are essentially free of mites, their eggs and apple scab disease. As a result of the excellent mite control, the sprayed trees have foliage of a thrifty, dark green color, and they exhibit good twig growth and fruit size.

| Example 19 | Percent |
|---|---|
| Methyl 4-(o-trifluoroacetamidophenyl)-3-thioallophanate | 60 |
| dialkylsulfosuccinate, sodium salt | 1 |
| sodium ligninsulfonate | 1 |
| diatomaceous silica | 38 |

The materials are combined, air milled twice, and then blended.

The formulation of this example is useful for the control of peach scab and brown rot caused by the fungi, *Cladosporium carpophilum* and *Monolinia laxa*. This is demonstrated by an orchard study in which random trees in a peach planting are sprayed to run off. Starting in the spring selected trees are sprayed from all sides with the formulation of this example at a rate of 300 ppm active ingredient in water. The same trees are sprayed each 14 days throughout the season. At harvest the trees receiving the treatment are heavily laden with large healthy peaches. On the other hand, the trees which did not receive the treatment had only a few fruit because of a severe blossom blight infection with brown rot, and those remaining fruit were severely spotted with scab lesions.

The following compounds are each substituted one at a time for the Methyl 4-(o-trifluoroacetamidophenyl)-3-thioallophanate above in like amount by weight. They are formulated and applied in like manner; like results are obtained.

Methyl 4-(o-acetamidophenyl)-3-thioallophanate
Methyl 4-(o-butyramidophenyl)-3-thioallophanate
Methyl 4-(o-acetoacetamidophenyl)-3-thioallophanate
Methyl 4-[o-(3-methylureido)phenyl]-3-thioallophanate
Methyl 4-(o-methoxycarbonylainophenyl)-3-thioallophanate
Methyl 4-(o-ureidophenyl)-3-thioallophanate
Methyl 4-[o-(3-methylthioureido)phenyl]-3-thioallophanate
Methyl 4-[o-(3-butylthioureido)phenyl]-3-thioallophanate

| Example 20 | Percent |
|---|---|
| Methyl 4-(o-acetamidophenyl)-3-thioallophanate | 70 |
| alkylbenzenesulfonic acid, sodium salt | 1 |
| sodium ligninsulfonate | 3 |
| diatomaceous silica | 26 |

The materials are combined, micropulverized, air milled, and then blended.

A uniform field planting of cantaloupe in North Carolina is inoculated with the powdery mildew fungus (*Erysiphe cichoracearum*). After 10 days this organism has become well established in the plants.

At this time alternate rows are sprayed with water containing a suspension of the wettable powder prepared as described above and an added amount of a polyhydric alcohol ester surface-active agent ("Trem" 014). The concentrations of this chemical suspension is such as to give 227 grams of the active compound of this formulation per 378 liters of water (600 ppm) and 400 ppm of the surfactant. The spray is applied at a volume of 1400 liters per hectare. The remaining rows are left unsprayed.

After aother 15 days the unsprayed rows are heavily damaged by powdery mildew and some of the plants are dying. The sprayed rows, however, are healthy and growing rapidly. The results indicate that the active compound of the suspension acts as a curative fungicide.

Any one of the following compounds may be substituted for the Methyl 4-(o-acetamidophenyl)-3-thioallophanate above in like amount by weight. When formulated and applied in like manner, like results are obtained.

Methyl 4-(o-ureidophenyl)-3-thioallophanate
Methyl 4-(o-trifluoroacetamidophenyl)-3-thioallophanate
Methyl 4-(o-methoxycarbonylaminophenyl)-3-thioallophanate
Methyl 4-(o-butyramidophenyl)-3-thioallophanate
Methyl 4-(o-acetoacetamidophenyl)-3-thioallophanate
Methyl 4-[o-(3-methylureido)phenyl]-3-thioallophanate
Methyl 4-[o-(3-methylthioureido)phenyl]-3-thioallophanate
Methyl 4-[o-(3-butylthioureido)phenyl]-3-thioallophanate

| Example 21 | Percent |
|---|---|
| Methyl 4-(o-acetamidophenyl)-3-thioallophanate | 60 |
| sucrose + impurities in technical active material | 36 |
| dioctylsulfosuccinate, sodium salt | 3 |
| low viscosity methyl cellulose | 1 |

The materials are combined, micropulverized, air milled and then blended.

Test plots are established in a rice field. The plots are sprayed with water containing a suspension of the wettable powder described above along with a polyhydric alcohol ester surface active agent ("Trem" 014). The amount of the wettable powder used is such as to provide 0.6 grams of the active compound of this invention per liter of water. The amount of Trem 014 is 400 ppm in the final spray and 600 ppm with respect to the active ingredient. The spray is applied at weekly intervals at the rate of 900 liters per hectare. The remainder of the field is left unsprayed. Three months after the start of the test, the sprayed plots are healthy and growing well. The untreated plots, on the other hand, are seriously damaged by the rice blast fungus, *Piricularia oryzae* which greatly reduces yield.

The following compounds may be substituted one at a time for the Methyl 4-(o-acetamidophenyl)-3-thioallophanate above in like amount by weight. They are formulated and applied in like manner; like results are obtained.

Methyl 4-(o-butyramidophenyl)-3-thioallophanate
Methyl 4-(o-acetoacetamidophenyl)-3-thioallophanate
Methyl 4-[o-(3-methylureido)phenyl]-3-thioallophanate
Methyl 4-(o-methoxycarbonylaminophenyl)-3-thioallophanate
Methyl 4-(o-ureidophenyl)-3-thioallophanate
Methyl 4-(o-trifluoroacetamidophenyl)-3-thioallophanate
Methyl 4-[o-(3-methylthioureido)phenyl]-3-thioallophanate
Methyl 4-[o-(3-butylureido)phenyl]-3-thioallophanate

| Example 22 | Percent |
|---|---|
| Methyl 4-(o-ureidophenyl)-3-thioallophanate | 5 |
| Kaolin | 5 |
| Sodium alkylbenzenesulfonate | 0.5 |
| Talc | 89.5 |

The active material, surfactant and kaolin are combined and ground and then mixed with the talc and blended.

A single row is selected in a suger beet field for treatment with the dust of this formulation. After the sugar beets are one month old and a few lesions of *Cercospora beticola* have become evident as spots on the leaves, weekly dust treatments are applied to the selected row. The 5% dust of this formulation is applied to a single row at approximately 30 kilograms per hectare. There is some drift to adjacent rows but the remainder of the field is left untreated. At harvest the foliage is examined and the beets are dug and weighed. The treated row is a vigorous healthy row with lush green foliage and the beets are large and normal. The adjacent rows are spotted with numerous leaf spot lesions and the remainder of the field is almost entirely defoliated. A few young leaves on the untreated beets are still green but all of the older leaves are dried up. Beets from the untreated rows are less than half normal size.

Any of the compounds of this invention can be formulated in like manner and applied with similar results.

| Example 23 | Percent |
|---|---|
| Wettable powder of Example 18 | 6 |
| Micaceous talc | 94 |

The above ingredients are blended to give a freely flowing dust.

This dust formulation is applied to individual vines of grapes in otherwise untreated rows in a vineyard. The applications are made at a rate of twenty kilograms per hectare at 14-day intervals for a period of three months during the growing season. At the end of the treatment period the treated vines are healthy, support a heavy crop of high quality fruit, and show evidence of excellent cane growth. The foliage and fruit of untreated vines are severely damaged by powdery mildew (*Uncinula necator*) and by Botrytis and other fruit rots.

Any of the wettable powders of Examples 19 – 21, incl., may be substituted for the wettable powder in Example 23. The resulting dusts are applied in like manner; similar results are obtained.

GRANULES

| Granules | |
|---|---|
| Example 24 | Percent |
| Sodium alkylnaphthalenesulfonate | 1 |
| Methyl 4-[o-(3-methylureido)phenyl]-3-thioallophanate | 25 |
| Anhydrous sodium sulfate | 10 |
| Calcium, magnesium bentonite | 59 |
| Calcium, magnesium ligninsulfonate | 5 |

The powdered active material and other ingredients are combined and moist granulated, dried and then screened to make a 20–80 mesh mixture.

A field in California is seeded with cotton in the normal manner, except that granules prepared as set forth above are added to alternate rows. These granules are dropped in such a way that some fall into the furrow and some are mixed with the covering soil. The rate of granule application is such as to employ 0.90 kilograms of active chemical of this invention per 3600 meters of row. The remaining rows are untreated.

Six weeks after planting, many of the plants in the rows without the granules are dead, and others show soreshin lesions caused by *Rhizoctonia solani* as well as heavy populations of the Pacific mite (*Tetranychus pacificus*). In the rows that had received the granules, all plants remain alive and are healthy, and further they are free of mites. The effect on mites is clearly systemic.

Any of the compounds of this invention may be substituted for the active ingredient above with similar results.

PELLETS

| Pellets | |
|---|---|
| Example 25 | Percent |
| Methyl 4-(o-acetoacetamidophenyl)-3-thioallophanate | 25 |
| calcium, magnesium bentonite | 64 |
| sodium sulfate, anhydrous | 10 |
| alkylnaphthalenesulfonic acid, sodium salt | 1 |

This composition is blended, moistened with water in a pug mill and then extruded and dried.

The pellets of this example may be applied in a manner similar to the granules of Example 24 with comparable results.

The following compounds are each substituted one at a time for the Methyl 4-(o-acetoacetamidophenyl)-3-thioallophanate above in like amount by weight. When formulated and applied in like manner, like results are obtained.

Methyl 4-[o-(3-methylureido)phenyl]-3-thioallophanate
Methyl 4-(o-methoxycarbonylaminophenyl)-3-thioallophanate
Methyl 4-(o-ureidophenyl)-3-thioallophanate
Methyl 4-(o-trifluoroacetamidophenyl)-3-thioallophanate
Methyl 4-(o-acetamidophenyl)-3-thioallophanate
Methyl 4-(o-butyramidophenyl)-3-thioallophanate
Methyl 4-[o-(3-methylthioureido)phenyl]-3-thioallophanate
Methyl 4-[o-(3-butylthioureido)phenyl]-3-thioallophanate

AQUEOUS DISPERSION

| Aqueous Dispersion | |
|---|---|
| Example 26 | Percent |
| Methyl 4-(o-butyramidophenyl)-3-thioallophanate | 30 |
| calcium, magnesium ligninsulfonate (goulac) | 15 |
| attapulgite, hydrated | 3 |
| disodium phosphate, anhydrous | 1 |
| dodecyl alcohol | 0.005 |
| water | 50.995 |

The dispersion is prepared by mixing the ingredients and sandmilling the mixture.

Six field crates of oranges are picked from a commercial grove in Florida. Three of these crates of oranges are dipped for 3 minutes in a water bath containing a suspension made from the above formulation, in an amount to give 300 parts per million by weight of the active ingredient of this invention. A polyethylene glycol ester of oleic acid surface active agent is present at the rate of 150 ppm of total liquid. The remaining three crates are dipped in a similar fashion in water with the surface-active agent only. All crates are set aside in a citrus storage house for three weeks. At the end of this time all fruits are examined. The fruit that has been dip-treated with the compounds of this invention is still in good condition, but the fruit that is not so protected is largely rotted by the blue mold fungus (*Penicillium digitatum*).

The other compounds of this invention may be similarly formulated and when used as above give like results.

OIL DISPERSION

| Oil Dispersion | |
|---|---|
| Example 27 | Percent |
| Methyl 4-(o-trifluoroacetamidophenyl)-3-thioallophanate | 25 |
| blend of polyalcohol carboxylic acid esters and sulfonated oils | 8 |
| isoparaffin oils (Soltrol 170) | 67 |

The dispersion is prepared by mixing the ingredients and sandmilling the mixture. The resulting dispersion can be sprayed as a concentrate, diluted with oil or emulsified in water and then applied.

The formulation of this example is useful for the control of Sigatoka disease fungus (*Mycosphaerella musicola*). This is demonstrated by a plantation study in which a plot showing the first visible yellow spots of the disease is sprayed from the air with an aqueous suspension of this formulation containing 454 grams of active ingredient at a rate of 454 grams in 45 liters of water per hectare. The adjacent plots, also showing signs of incipient disease, are left untreated. At harvest the foliage is examined and representative samples of fruit weighed. The untreated plots show severely damaged leaves and prematurely ripened, small, unmarketable bananas. The treated plot yields heavy well-developed bananas from vigorous undiseased plants.

The following compounds may be substituted one at a time for the Methyl 4-(o-trifluoromethylacetamidophenyl)-3-thioallophanate above in like amount by weight. When formulated and applied in like manner, like results are obtained.

Methyl 4-(o-acetamidophenyl)-3-thioallophanate
Methyl 4-(o-butyramidophenyl)-3-thioallophanate
Methyl 4-(o-acetoacetamidophenyl)-3-thioallophanate
Methyl 4-[o-(3-methylureido)phenyl]-3-thioallophanate
Methyl 4-(o-methoxycarbonylaminophenyl)-3-thioallophanate
Methyl 4-(o-ureidophenyl)-3-thioallophanate
Methyl 4-[o-(3-methylthioureido)phenyl]-3-thioallophanate
Methyl 4-[o-(3-butylthioureido)phenyl]-3-thioallophanate

AQUEOUS SOLUTION

| Aqueous Solution | |
|---|---|
| Example 28 | Percent |
| Methyl 4-[o-(3-methylureido)phenyl]-3-thioallophanate | 10 |
| Sodium hydroxide | 1.75 |
| Methanol | 20 |
| Water | 68.25 |

The above ingredients are stirred together until a homogeneous solution results.

A single row is selected in a sugar beet field for treatment with the solution of this formulation. After the sugar beets are one month old and several lesions of *Cercospora beticola* have become evident as spots on the leaves, weekly treatments are applied to the selected row. The 10% aqueous solution of this formulation is applied to a single row at approximately 200 grams of the active ingredient per hectare. There is some drift to adjacent rows but the remainder of the field is left untreated. At harvest the foliage is examined and the beets are dug and weighed. The treated row is a vigorous healthy row with lush green foliage and the beets are large and normal, clearly demonstrating the eradicant or curative nature of this treatment. The adjacent rows are spotted with numerous leaf spot lesions and the remainder of the field is almost entirely defoliated. A few young leaves on the untreated beets are still green but all of the older leaves are dried up. Beets from the untreated rows are less than half normal size.

WATER SOLUBLE POWDER

| Water Soluble Powder | |
|---|---|
| Example 29 | Percent |
| Potassium salt of methyl 4-[o-3-methylureido)phenyl]-3-thioallophanate | 99 |

| Water Soluble Powder | |
|---|---|
| Example 29 | Percent |
| Finely divided silica | 1 |

The above ingredients are blended and passed through a 40 mesh screen.

Six field crates of oranges are picked from a commercial grove in Florida. Three of these crates of oranges are dipped for 3 minutes in a water bath containing a solution made from the above formulation, in an amount to give 300 parts per million by weight of the active ingredient of this invention. A polyethylene glycol ester of oleic acid surface-active agent is present at the rate of 150 ppm of total liquid. The remaining three crates are dipped in a similar fashion in water with the surface-active agent only. All crates are set aside in a citrus storage house for three weeks. At the end of this time all fruits are examined. The fruit that has been dip-treated with the compounds of this invention is still in good condition, but the fruit that is not so protected is largely rotted by the blue mold fungus (*Penicillium digitatum*).

I claim:

1. The method of preventing injury due to mites or fungi consisting essentially of applying to the locus to be protected from fungi and mites a fungicidally and mite ovicidally effective amount of a compound of the formula:

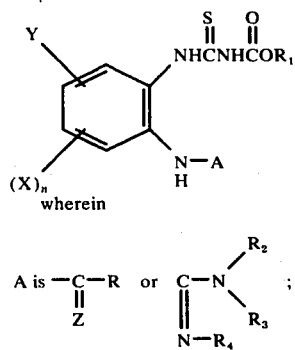

wherein

A is 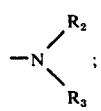

X is hydrogen, fluorine, chlorine, or bromine;
Y is hydrogen or alkyl of 1 to 4 carbon atoms;
$R_1$ is alkyl of 1 to 12 carbon atoms;
Z is oxygen or sulfur;
R is hydrogen, alkyl of 1 to 12 carbon atoms, alkyl of 1 to 12 carbon atoms substituted with fluorine, chlorine, bromine, alkoxy of 1 to 3 carbon atoms or acetyl; alkoxy of 1 to 4 carbon atoms; or

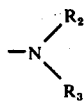

$R_2$ is hydrogen or methyl;
$R_3$ is hydrogen or alkyl of 1 to 4 carbon atoms;
$R_4$ is hydrogen or methyl;
When y is alkyl, n is O and when Y is hydrogen, n is 1, 2, or 3; and the sodium, potassium, lithium, calcium, barium, copper, zinc and manganese salts of these compounds.

2. The method of claim 1 wherein A is

and Z is sulfur.

3. The method of claim 1 wherein A is

Z is sulfur, X and Y are hydrogen and $R_1$ methyl, ethyl or isopropyl.

4. The method of claim 1 consisting essentially of applying a fungicidally and mite ovicidally effective amount of methyl 4-[o-(3-methylthioureido)phenyl]-3-thioallophanate.

5. The method of claim 1 consisting essentially of applying a fungicidally and mite ovicidally effective amount of methyl 4-[o-(3-butylthioureido)phenyl]-3-thioallophanate.

6. A mite ovicidal or fungicidal composition comprising a suitable inert diluent with a fungicidally and mite ovicidally effective amount of a compound of the formula

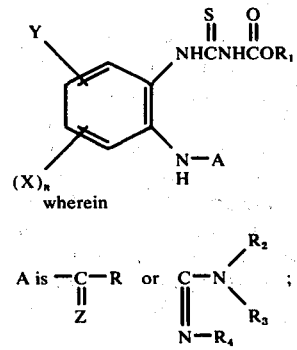

wherein

A is 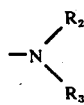

X is hydrogen, fluorine, chlorine, or bromine;
Y is hydrogen or alkyl of 1 to 4 carbon atoms;
$R_1$ is alkyl of 1 to 12 carbon atoms;
Z is oxygen or sulfur;
R is hydrogen, alkyl of 1 to 12 atoms, alkyl of 1 to 12 carbon atoms substituted with fluorine, chlorine, bromine, alkoxy of 1 to 3 carbon atoms or acetyl;

alkoxy of 1 to 4 carbon atoms; or $R_2$ is hydrogen or methyl;
$R_3$ is hydrogen or alkyl of 1 to 4 carbon atoms;

$R_4$ is hydrogen or methyl;

When Y is alkyl, $n$ is 0 and when Y is hydrogen, $n$ is 1, 2, or 3; and the sodium, potassium, lithium, calcium, barium, copper, zinc and manganese salts of these compounds.

7. The mite ovicidal or fungicidal composition of claim 6 wherein A is

8. The mite ovicidal or fungicidal composition of claim 6 wherein A is

X and Y are hydrogen and $R_1$ is methyl, ethyl or isopropyl.

9. The mite ovicidal or fungicidal composition of claim 6 comprising a suitable inert diluent with a fungicidally and mite ovicidally effective amount of the compound 4-[o-(3-methylthioureido)phenyl]-3-thioallophanate.

10. A mite ovicidal or fungicidal composition of claim 6 comprising a suitable inert diluent with a fungicidally and mite ovicidally effective amount of the compound 4-[o-(3-butylthioureido)phenyl]-3-thioallophanate.

* * * * *